US005155039A

United States Patent [19]
Chrisope et al.

[11] Patent Number: 5,155,039
[45] Date of Patent: Oct. 13, 1992

[54] APPARATUS FOR METHODS FOR PRESERVING, TRANSPORTING STORING, RE-HYDRATING AND DELIVERING VIABLE MICRO-ORGANISMS

[75] Inventors: Gerald L. Chrisope; Nell C. Roberts, both of Lake Charles, La.

[73] Assignee: Chrisope Technologies, Inc., Lake Charles, La.

[21] Appl. No.: 733,698

[22] Filed: Jul. 22, 1991

[51] Int. Cl.⁵ ............................................. C12N 1/00
[52] U.S. Cl. .................................. 435/243; 435/260; 435/296; 435/297; 435/298; 435/810
[58] Field of Search ................... 439/2, 243, 260, 296, 439/297, 298, 300, 810

[56] References Cited

U.S. PATENT DOCUMENTS

| | | | |
|---|---|---|---|
| 3,075,887 | 1/1963 | Silliker et al. | 435/260 X |
| 3,147,197 | 9/1964 | Connors . | |
| 3,671,400 | 6/1972 | Cekoric, Jr. et al. | 195/100 |
| 3,843,456 | 10/1974 | Haden et al. . | |
| 4,010,077 | 3/1977 | Pardos | 195/127 |
| 4,217,419 | 8/1980 | Suzuki | 435/253 |
| 4,217,420 | 8/1980 | Langejan | 435/256 |
| 4,234,316 | 11/1980 | Hevey | 23/230 R |
| 4,672,037 | 6/1987 | Daggett et al. | 435/253 |
| 4,800,156 | 1/1989 | Yuhda | 435/296 |
| 4,830,970 | 5/1989 | Madaus et al. | 435/296 |
| 4,885,253 | 12/1989 | Kravlovic | 435/296 |

FOREIGN PATENT DOCUMENTS

| | | |
|---|---|---|
| 684065 | 12/1977 | U.S.S.R. . |
| 8900189 | 1/1989 | World Int. Prop. O. ........... 435/260 |

OTHER PUBLICATIONS

Culti-Loop Brochure (2 page), 1984.
Cult-Loop Device.

Primary Examiner—Robert J. Warden
Assistant Examiner—Krisanne M. Thornton
Attorney, Agent, or Firm—Browning, Bushman, Anderson & Brookhart

[57] ABSTRACT

The present invention is directed to systems and methods for preserving, transporting, storing, re-hydrating and delivering viable micro-organisms. More particularly, the present invention is directed to a kit and method for preserving and storing dried, microbiological organisms and for re-hydrating and delivering specific and reproducible numbers of viable organisms therefrom. The kit and method of the present invention provides the capability to deliver a known quantity of rehydrated micro-organisms as a single, total dose of cells without the inaccuracies and safety hazards associated with standard needle, syringe or pipette transfer systems. The kit includes first and second vial and cap combinations, the first carrying the dried organisms in a dry, biologically inert atmosphere, the second carrying a pre-measured quantity of re-hydrating fluid. A quantitative number of selected microbiological organisms are dried under mild conditions, i.e., ambient temperature and pressure using forced air flow, to fixative sites on the underside of the first cap engaged in sealing relation with the first vial. Transfer of that cap to the second vial containing the re-hydrating fluid provides easy re-hydration and the ability to deliver specific and reproducible numbers of viable organisms after extended storage periods at normal refrigeration temperatures.

20 Claims, 1 Drawing Sheet

APPARATUS FOR METHODS FOR PRESERVING, TRANSPORTING STORING, RE-HYDRATING AND DELIVERING VIABLE MICRO-ORGANISMS

BACKGROUND OF THE INVENTION

1. Field of the Invention

The present invention generally relates to a system and method for preserving, transporting, storing, re-hydrating and delivering viable micro-organisms. More particularly, the present invention is directed to a kit and method for preserving and storing dried, microbiological organisms and for re-hydrating and delivering specific and reproducible numbers of viable organisms, most preferably as a single, total dose of cells.

2. Description of the Background

The quantitative determination of the number of pathogenic and/or indicator micro-organisms in a sample is as important in many public health applications as the mere determination of the presence or absence of those organisms. The infective dose, i.e., the number of micro-organisms required to produce infection in the host, has been determined for many species. Although strain dependent, the infective dose may vary from as few as ten organisms of *Shigella dysenteriae* to as many as one hundred million or more for *Salmonella typhosa* or *Vibrio cholerae*.

In other applications, the wholesomeness or sanitary quality of food, milk, other dairy products, shellfish, potable water, shellfish growing waters, waste waters and a variety of surface waters is determined by the quantitative enumeration of specific indicator organisms.

The federal Food and Drug Administration (FDA) has equally stringent requirements and regulations controlling the microbial purity, i.e., sterility and effectiveness, of microbial preservatives in food, drugs, and cosmetics for human consumption and/or use.

There are many other applications in the clinical and veterinary fields for a product which provides specific and reproducible quantities of viable micro-organisms. For example, the Centers for Disease Control (CDC) in Atlanta, Ga. require both inhibition of quantitative challenge doses of saprophytic micro-organisms and recovery of quantitative doses of *Neisseria gonorrhoeae* and *Neisseria meningitis* by highly selective culture media such as Thayer Martin Agar and its modifications.

Federal and state statutes specifically provide precise requirements for methodology, equipment, facilities, quality assurance plans and quality control of analytical techniques, materials and individual analyst precision.

There has been a long felt but unfulfilled need in all the foregoing markets to evaluate the performance of techniques, materials and analysts using a product which will provide a specific and reproducible number of viable micro-organisms in a ready-for-use design.

While there are many commercial sources of standard micro-organisms available in viable states, there are no guarantees, implied or explicit, of the numbers of organisms present. Currently available methods for preserving micro-organisms have typically employed harsh conditions, e.g., vacuum lyophilization and storage at temperatures well below $-20°$ C. When subjected to these severe preservation and storage conditions no products have been capable of providing known and reproducible numbers of viable organisms. One attempt to solve this problem included the lyophilization of a specified count of cultures in a serum vial. Rehydration and transfer of the cultures in this vial required the use of a needle to dispense rehydration fluid followed by use of another needle and syringe to withdraw defined aliquots of solution to deliver a known count of cultures. The vial served as a reservoir and the system depended on the accuracy of the individual user to measure the rehydrating fluid, to properly mix the lyophilized culture and rehydrating fluid and to withdraw the defined aliquots. In addition to all of the possibilities for introduction of errors in this process, this method suffered from many opportunities for contamination of both the environment and the user resulting from the use of various needles, syringes or pipettes.

Because the foregoing sources have been unacceptable, the current state of the art for the aforementioned procedures requiring specific numbers of control micro-organisms has required on-site preparation of estimated doses of living micro-organisms. These processes require one or more transfers of the microbes, time for adequate growth to appear and subsequent preparation of a suspension containing an appropriate number of viable cells. There is no practical way to determine in advance the number of colony forming units. The process requires considerable skill, time and money to achieve and is as much art as science. These suspensions have relatively short shelf lives ranging from a few minutes to a maximum of 24 to 48 hours. Accordingly, there has been a long felt but unfulfilled need for a system of providing specific and reproducible numbers of viable micro-organisms in a safe and readily usable form.

SUMMARY OF THE INVENTION

The present invention is directed to systems and methods for preserving, transporting storing, re-hydrating and delivering specific and reproducible numbers of viable micro-organisms, most preferably as a single, total dose of cells. More particularly, the system is directed to a kit having a first vial and cap combination and including on fixative sites on the underside of the cap dried microbiological organisms. The vial both contains and is surrounded by a dry, biologically inert atmosphere, typically merely an oxygen-free atmosphere. In the method of the present invention the vial and cap combination is prepared by disposing on the fixative sites a liquid containing the microbiological organisms, drying that liquid under mild conditions, i.e., ambient temperature and pressure preferably using a forced air flow, to aid survivability of the micro-organisms and sealing the cap to a vial previously purged of oxygen or any other biologically undesirable gas and containing a desiccant. Preferably the vial further includes a barrier to prevent contact of the desiccant with the dried micro-organisms. In a more preferred embodiment of the present invention, this first vial and cap combination, including the dried microbiological organisms, is sealed within a second packaging material in a dry, biologically inert atmosphere, preferably a metallic foil or plastic film, e.g., conventional mylar packaging material.

The kits of the presently preferred embodiment further include a second vial and cap combination having disposed therein a pre-measured quantity of a liquid suitable for re-hydrating the dried micro-biological organisms disposed on the first cap. The vials and caps of the kit are constructed so that the caps are interchangeable. Because the cap containing the dried organisms is sealingly engageable with the vial containing the re-hydrating fluid, the dried organisms may be easily re-hydrated by transferring the cap containing those organisms to the vial containing the re-hydrating fluid and inverting to bring the fluid into contact with the dried organisms. In fact, these steps comprise the method of the present invention for re-hydrating dried microbiological organisms preserved and stored in accord with the previously described method. Once rehydrated, the organisms may be delivered as a single, total dose of cells.

When a known quantity of viable micro-organisms is disposed on the fixative sites of the first cap, dried using the specified mild conditions and sealed in a dry, biologically inert atmosphere, the resulting dried organisms may be transported and stored for extended periods at normal refrigeration temperatures. More importantly, because of the mild processing and storage conditions, a specific and reproducible number of viable micro-organisms may be delivered for use in subsequent tests.

The kit and methods of the present invention provide easily manufactured, transported, stored and used means for preserving and later re-hydrating microbiological organisms. In fact, the kit of the present invention permits the preservation and storage for extended periods at normal refrigeration temperatures of microbiological organisms which previously were preserved by drying in harsh conditions, e.g., lyophilization, and could not be stored for extended periods except at extremely low temperatures, e.g., less than −20° C.

BRIEF DESCRIPTION OF THE DRAWINGS

Other features and intended advantages of the invention will be more readily apparent by the references to the following detailed description in connection with the accompanying drawings, wherein.

Figure 1:
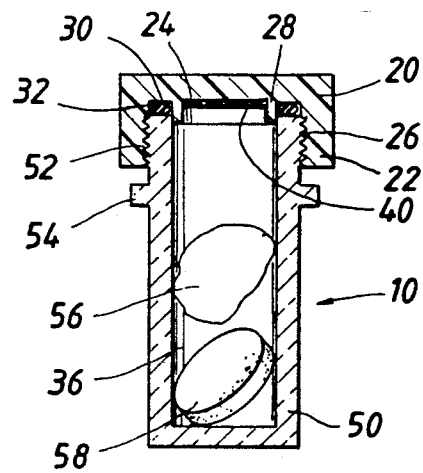
FIG. 1 is a side cross-sectional illustration of a first vial and cap combination including fixative sites with dried micro-organisms affixed thereto in a dry, biologically inert atmosphere in accord with the present invention.

While the invention will be described in connection with the presently preferred embodiments, it will be understood that it is not intended to limit the invention to these embodiments. On the contrary, it is intended to cover all alternatives, modifications and equivalents as may be included within the spirit of the invention as defined in the appended claims.

DETAILED DESCRIPTION OF THE PREFERRED EMBODIMENT

The kit 100 of the present invention comprises a first vial 10 having therein dried microbiological organisms 40 and a second vial 110 having therein a pre-measured quantity of re-hydrating fluid 140. First vial 10 and second vial 110 are illustrated, respectively, in FIGS. 1 and 3, while the kit 100 of the present invention is illustrated in FIG. 4.

With reference to FIG. 1, a first, sealable vial and cap combination 10 comprises a vial 50 together with a cooperating cap 20. Cap 20 is sealingly engageable with vial 50 by any conventional construction. Preferably and for safety reasons, vial 50 and cap 20 are constructed from a conventional, preferably hard, plastic. However, in an alternative, less preferred embodiment, any appropriate vial and cap material, such as glass, metal or the like may be employed. In the preferred embodiment, vial 50 is comprised of a sterile plastic, e.g., polyethylene, polypropylene or another polymeric material. For convenience in manipulation vial 50 includes grip ring 54. Vial 50 is provided with threads 52 about its exterior open end.

Figure 2:
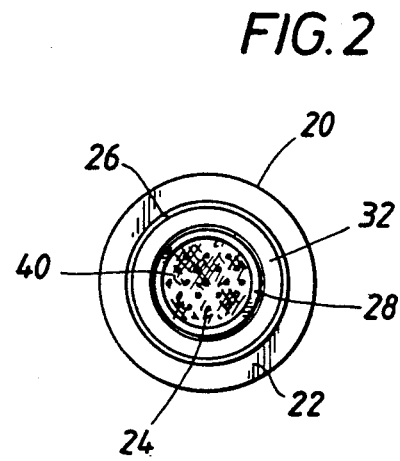
FIG. 2 is an elevation looking into the bottom of the cap of FIG. 1 illustrating the underside of the cap having fixative sites with dried micro-organisms affixed thereto in accord with the present invention.

With reference to FIGS. 1 and 2, the underside of cap 20 includes about the periphery thereof a rim 22 with interior facing threads 26 for engagement with threads 52 of vial 50. The underside of cap 20 is further characterized by protruding, circular lip 28. Lip 28, together with rim 22 define a groove 32 for receiving an elastomeric O-ring, washer or other sealing device 30 for cooperation with the end of vial 50 to ensure sealing engagement between vial 50 and cap 20. Lip 28 also defines on the interior thereof an area having a plurality of fixative sites 24, preferably irregularities to which are adhered microbiological organisms such as those illustrated in film 40. Fixative sites 24 may be formed on the interior surface of cap 20 by abrading, scoring, scratching, or otherwise marring the surface with any appropriate instrument or means to produce an irregular, unsmooth surface to aid adhesion of the dried microbiological organism film 40. One convenient method of forming acceptable irregularities includes the scoring of surface 24 with an electrical drill bit. In a more preferred embodiment, at least the underside of cap 20 is comprised of a plastic material, pre-molded with irregular, rough fixative sites 24.

The film 40 of dried microbiological organisms may be produced by disposing a known volume of liquid containing a known quantity of viable organisms onto the inverted cap 20 within the circumscribed area of fixative sites 24 surrounded by retaining lip 28. Subsequent evaporation and drying produces the illustrated film 40 of microbiological organisms. Preferred methods are described in more detail below.

Vial 50 preferably further includes a conventional desiccant, e.g., tablet 58, together with a sterile barrier, e.g., cotton insert 56, to prevent contact between the desiccant 58 and film 40 of dried microbiological organisms.

The interior 36 of the sealed vial 50 and cap 20 combination 10 is provided with a dry, biologically inert atmosphere, preferably an oxygen-free atmosphere. This atmosphere aids in preservation of viable, dried organisms. Those skilled in the art are aware of many methods for producing such an atmosphere. While creation of a vacuum might be acceptable, the preferred methods of the present invention include flushing of the interior 36 of vial 50 with a biologically inert gas and sealing with an atmosphere of the flushing gas. While any biologically inert gas may be used, the preferred gases include nitrogen and the noble gases, i.e., helium, argon, neon and the like. Because of cost and convenience nitrogen is the preferred gas used for flushing and for providing the desired biologically inert atmosphere.

Finally, in the preferred embodiment illustrated in FIG. 4, vial 50 containing a film 40 of dried organisms is, itself, sealed in a biologically inert atmosphere of the type previously described in a second packaging 104, preferably a non-breakable packaging such as a mylar or metallic film pouch 102.

Figure 3:
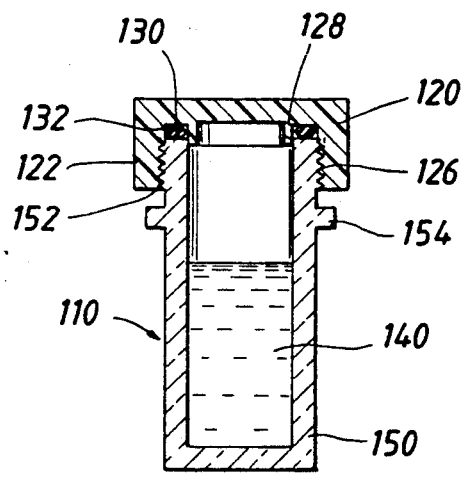
FIG. 3 is a side cross-sectional illustration of a second vial and cap combination in accord with the present invention and including therein a pre-determined quantity of a re-hydrating liquid.
Figure 4:
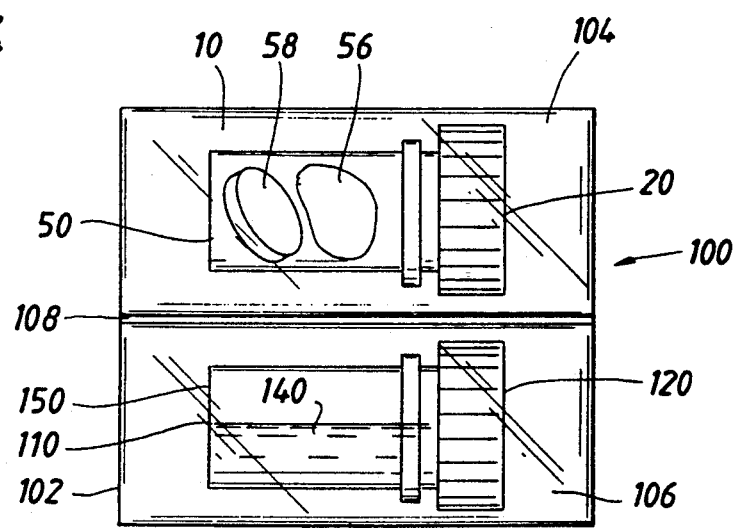
FIG. 4 is an elevational illustration of a kit in accord with the present invention including a first vial containing dried microbiological organisms and a second vial containing a pre-measured quantity of re-hydrating fluid, both disposed in separate, sealed compartments of a mylar packaging pouch.

Vial and cap combination 110 for holding a pre-measured quantity of re-hydrating fluid 140 is illustrated in FIG. 3. Combination 110 includes a vial 150 substantially identical to vial 50 in all respects and sealingly engageable both with cap 120 and with cap 20. Vial 150 includes grip ring 154 and exterior facing threads 152 about its open end. Cap 120 is substantially similar to cap 20 with the exception that the central portion of the underside of cap 120 may be smooth because there is no need for fixative sites 24. Cap 120 is characterized by upset rim 122 about the periphery thereof with threads 126 on its interior surface for cooperation with threads 152 of vial 150. Cap 120 further includes upset lip 128 to form groove 132 with the lower portion of rim 122 for receiving a conventional sealing means, e.g., an elastomeric O-ring, conventional elastomeric washer or other seal means 130. The type and quantity of re-hydrating fluid 140 is chosen for compatibility with the dried micro-organisms in film 40 on cap 20 of the associated first vial and cap combination 10. Those skilled in the art are knowledgeable of the type and quantity of re-hydrating liquid to be used for any given organism. Examples of common re-hydrating liquids are provided below.

In the preferred embodiment, second vial and cap combination 110 containing re-hydrating fluid 140 is disposed in a second portion 106 of pouch 102. In the preferred embodiment of kit 100, pouch 102 has been sealed at 108 to provide a first pouch portion 104 for receiving vial and cap combination 10 containing a film 40 of dried micro-organisms and a second pouch portion 106 for receiving vial and cap combination 110 containing the associated pre-measured quantity of re-hydrating fluid.

Cap 20 upon which has been disposed a film 40 of dried microbiological organisms is interchangeable with cap 120. Accordingly, rehydration of the dried organisms is easily achieved by transfer of cap 20 containing film 40 to vial 150 containing fluid 140 and inversion to bring the re-hydrating fluid 140 into contact with the dried micro-organisms.

In the preferred embodiment, a known quantity of micro-organisms have been dried onto fixative sites 24 in film 40 under mild conditions, i.e., ambient temperature and pressure and preferably using a simple forced air flow. By maintaining the micro-organisms in a dry, biologically inert atmosphere in cavity 36 and further protected from biologically active gases, e.g., oxygen or carbon dioxide, by maintaining vial and cap combination 10 within a biologically inert atmosphere in pouch 104, the micro-organism may be maintained for extended periods at normal refrigeration temperatures, thus avoiding harsh preservation and storage conditions at extremely low temperatures. All of these steps help ensure viability of a high percentage of the originally dispensed micro-organisms so that upon re-hydration a specific and reproducible number of viable, re-hydrated micro-organisms may be provided for use in standarized laboratory testing procedures.

The following is a more detailed description of methods in accord with the present invention useful for preserving and rehydrating microbiological organisms, particularly quantitative numbers thereof.

Using conventional methods generally known to those skilled in the art, young micro-organisms in the logarithmic growth phase are harvested and diluted to a predetermined end point for the desired number of organisms. A preservative reagent solution of a formulation appropriate to each particular strain of microorganism must be used and will be well known to those skilled in the art. These reagent solutions typically comprise biologically acceptable additives or preservatives such as carbohydrates, proteins, reducing agents, toxin neutralizing agents, cryoprotective agents and the like.

These micro-organism preservative reagent mixtures are dispensed in carefully measured amounts to the fixative sites 24 defined by lip 28 in the previously prepared and sterilized caps 20. The precise number of viable micro-organisms may be determined by enumeration using standard micro-biological procedures which require a growth of the micro-organisms on appropriate culture media under standard conditions of temperature and atmosphere. During the dispensing step, a minimum of five aliquots representing the beginning, middle and end portions of the run should be selected at random for enumeration of colony forming units by standard procedures prior to the desiccation step. The remaining micro-organism preservative suspensions are dried to a steady weight in a forced air desiccant chamber optionally containing silica gel or another desiccant material. The forced air desiccant chamber should avoid extreme temperature conditions and should operate under mild, preferably ambient conditions, most preferably at a temperature from about 24° C. to about 32° C. Drying times under the preferred conditions average from about 4 to about 5 hours.

Vial 50 is fitted with cotton plug 56 or another optional barrier material comprised of any suitable, biologically inert, porous material. Immediately prior to use the vials are loaded with a desiccant, preferably in the form of a molecular sieve caplet 58, or any other conventional, biologically acceptable desiccant, e.g., silica gel.

Vials 50 containing film 40 of dried microbiological organisms must be filled with a dry atmosphere substantially free of any gas used in the growth or decay of the chosen organisms, e.g., oxygen or carbon dioxide, to provide the best preservation and viability of the organisms. Such an atmosphere may be referred to as a biologically inert atmosphere and the gases therein as biologically inert gases. In the preferred methods, the vials are flushed with any dry, biologically inert gas. While the noble gases or mixtures thereof might be used, nitrogen is the preferred gas. Alternatively, but in a much less preferred embodiment, the vials might be evacuated to provide the required dry, biologically inert atmosphere. The caps 20 containing the film 40 of dried microbiological organisms are then applied to and sealed to the vial 50 containing the dry, biologically inert atmosphere, and preferably a desiccant and sterile barrier to separate the desiccant from the film.

The assembled vial and cap combination 10 is then packaged and sealed in a non-breakable envelope 102, preferably in a first half 104 thereof which has also been provided with a dry, biologically inert atmosphere such as in the manner discussed above. Again, flushing with nitrogen gas is the preferred method. Finally, pouch 104 may also contain an additional desiccant (not shown) to aid in maintaining the desired dry atmosphere.

Examples of re-hydrating fluids include Butterfield's phosphate buffer for rehydration of *Enterobacteriaceae, Enterococcus*, yeast and a variety of other non-fastidious Gram positive and Gram negative micro-organisms. More nutrient-containing formulas, e.g., trypticase soy broth, may be used for more fastidious organisms. Formulations such as thioglycollate broth may be used for anaerobic micro-organisms. Other suitable re-hydration fluids are well known to those skilled in the art for any variety of selected micro-organism.

In order to quantitatively determine the number of viable micro-organisms available in the methods of the present invention, the following exemplary procedure may be employed. A minimum of five (5) aliquots selected at random from the dried, assembled kits are analyzed immediately after preparation for viable colony forming units as previously discussed. The cap containing the micro-organisms is screwed on and sealed to the re-hydrating fluid vial. The newly assembled combination containing the micro-organisms and re-hydrating fluid is inverted to allow contact between the dried micro-organisms and the re-hydrating fluid. The inverted combination is warmed for about ten (10) minutes at about 35° C. to about 37° C. to ensure complete solution of the dehydrated micro-organisms. No extra equipment or laboratory apparatus is required to re-hydrate and transfer the micro-organisms to culture media. No enrichment step, subcultures or estimation of the number of colony forming units is required. The produced suspension is ready for use in any procedure selected at the option of the analyst. For example, the entire contents may be decanted directly onto prepared agar medium for the spread plate method, into a sterile petri dish for the pour plate method, or into a dilution blank which may be examined by the membrane filter, multiple tube or most probable number method. While these and other tests are well known to those skilled in the art, detailed descriptions of some exemplary tests may be found in the literature. Exemplary references include *Standard Methods for the Examination of Water and Wastewater*, 17th Edition (1989) and *Standard Methods for Dairy Products*, 15th Edition (1985) both published by the American Public Health Association and the *Protocol and Producer Protocol for Testing Thayer Martin Media*, published by the Centers for Disease Control.

In the prior art methods for the preservation of micro-organisms, very high numbers of living micro-organisms are added to the preservation formulation to compensate for the unpredictable loss of viability known to occur. However, when using the apparatus and methods of the present invention, no significant change in viable colony counts during the dehydration process, storage at ordinary refrigeration temperatures, transport at ambient temperatures and re-hydration has been observed. For example, *Escherichia coli* has been used in a recently completed field trial experiment of the apparatus and method of the present invention. Results of colony counts of five (5) aliquots analyzed by the conventional spread plate method prior to drying for this lot were 30, 34, 37, 43 and 49. The statistical analysis of these data reveal a logarithmic mean of 38 colonies with a standard deviation of 0.075 and a variance of 0.006. In the experiment, the apparatus and methods of the present invention were employed to provide the dehydrated organisms in kits in accord with the present invention. After storage for fourteen (14) weeks at normal refrigeration temperatures, kits were shipped at ambient temperatures to seven (7) different laboratories. These laboratories re-hydrated the micro-organisms in accord with the methods of the present invention and analyzed the resulting solutions for viable organisms. Each laboratory examined five (5) aliquots by the membrane filtration technique for coliforms utilizing m-endo agar incubated for 24 hours at 35° C. Test results are reported in the following table.

TABLE 1

| LABOR-ATORY | MEAN* | STD. DEV. | VARIANCE | COLONY COUNT RANGE |
|---|---|---|---|---|
| 1 | 35 | 0.058 | 0.003 | 30–42 |
| 2 | 27 | 0.084 | 0.007 | 20–34 |
| 3 | 28 | 0.034 | 0.001 | 25–31 |
| 4 | 21 | 0.128 | 0.016 | 15–35 |
| 5 | 46 | 0.053 | 0.003 | 39–52 |
| 6 | 24 | 0.041 | 0.002 | 21–28 |
| 7 | 32 | 0.053 | 0.003 | 28–40 |

*Statistical analyses were performed using logarithmic transformed data from the individual sample colony counts obtained from each of the participating laboratories. Means and colony count ranges are stated as antilogarithms.

Desirable reproducibility is achieved with a logarithmic variance equal to or less than 0.012, the accepted logarithmic variance set by the FDA for certified analysts performing standard plate counts on normal milk samples. Six of the seven laboratories reported results having a variance between 0.001 and 0.007 with five of seven laboratories having variance less than or equal to 0.003. This test confirms the ability of the present apparatus and methods to deliver specific and reproducible numbers of viable organisms within acceptable statistical variance.

While the exact shelf life of quantitated micro-organisms preserved and re-hydrated in accord with the present invention is the object of ongoing studies, no statistically significant change in viability or colony counts has been observed in at least the first four months of this study. Current shelf life studies are designed to follow single lots of different strains of micro-organisms for up to eighteen months or until a significant change occurs in the viable populations. No significant changes have yet been observed.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described apparatus and methods may be made without departing from the scope and spirit of the invention. Therefore, the invention is not restricted to the particular form of construction and method illustrated and described, but covers all modifications which may fall within the scope of the following claims.

It is Applicant's intention the following claims to cover all modifications and variations which fall within the true spirit and scope of the invention.

What is claimed is:

1. A kit for storing at normal refrigeration temperatures dried microbiological organisms and for re-hydrating for delivery viable organisms, comprising: a first, sealable vial and cap combination, said first combination including a first cap having an underside;

fixative sites on said underside of said cap comprising surfaces to which microbiological organisms will adhere;

dried microbiological organisms disposed on said fixative sites;

a first vial for sealing cooperation with said first cap so that said fixative sites are sealed within said vial by said cap;

a desiccant disposed in said first vial, said desiccant physically separated from said dried organisms; and the interior of said sealable vial and cap combination filled with a dry, biologically inert atmosphere; a second, sealable vial and cap combination, said second combination including a second cap;

a second vial for sealing cooperation with said second cap; and a pre-measured quantity of a re-hydrating liquid disposed in said second vial; and wherein said first cap including said dried microbiological organisms is interchangeable with said second cap and sealingly engageable with said second vial including said pre-measured re-hydrating liquid to permit re-hydration of said dried organisms upon sealing engagement of said first cap with said second vial and inversion to contact said liquid with said dried organisms.

2. The kit of claim 1 wherein said dried microbiological organisms are present in a pre-measured quantity.

3. The kit of claim 1 wherein said fixative sites are formed by a plurality of irregularities on the underside of said first cap.

4. The kit of claim 3 wherein said fixative sites comprise irregularities selected from the group consisting of abrasions, scoring, scratches or other marring on the surface of said underside of said first cap.

5. The kit of claim 1 wherein said vials and caps are non-breakable.

6. The kit of claim 5 wherein said vials and caps are plastic.

7. The kit of claim 1 further including a packaging for holding said first and second vial and cap combinations.

8. The kit of claim 7 wherein at least the portion of said packaging holding said first vial and cap combination including said dried microbiological organisms is filled with a dry, biologically inert atmosphere.

9. The kit of claim 8 wherein said first and second vial and cap combinations are disposed in separate sealed portions of said packaging.

10. The kit of claim 9 wherein said packaging is non-breakable.

11. The kit of claim 10 wherein said packaging is selected from the group consisting of metallic foils and plastic films.

12. The kit of claim 11 wherein said first and second vial and cap combinations are plastic and said packaging is a mylar pouch, said pouch having two, distinct and separate compartments, a first compartment for receiving said first combination and a second compartment for receiving said second combination, said first compartment filled with a dry, biologically inert atmosphere.

13. The kit of claim 12 wherein said biologically inert atmosphere is oxygen free.

14. The kit of claim 1 wherein said vials and caps are threaded with cooperating threads and include means for sealing.

15. The kit of claim 1 further including a physical barrier of a biologically inert material disposed within said first vial to separate said desiccant from said dried organisms.

16. A method of preserving a sample of a microbiological organism, comprising:

dispensing a liquid including viable microbiological organisms onto fixative sites on the underside of a threaded cap, said sites comprising surfaces to which said organisms will adhere;

evaporating said liquid and drying said organisms to said fixative sites;

sealing said cap to a vial with said fixative sites sealed within said vial and cap combination, said vial having been purged of oxygen and containing a desiccant and sterile barrier to prevent contact of said desiccant with said dried microbiological organisms; and sealing said combination within a non-breakable packaging material, said packaging material also having been purged of biologically active gases before sealing.

17. The method of claim 16 wherein a known quantity of said viable organisms is dispensed onto said fixative sites.

18. The method of claim 16 wherein said evaporating and drying occurs at ambient temperatures and pressures.

19. The method of claim 18 wherein said evaporating and drying occurs with forced air flow.

20. A method of re-hydrating a dried microbiological organism prepared and stored in accord with the method of claim 19, comprising:

removing said combination from said packaging material;

removing said threaded cap to which said organisms have been dried from said vial;

sealing said threaded cap to a second vial containing a pre-measured quantity of a liquid suitable for re-hydrating said dried organisms; and inverting said cap and second vial to contact said dried organisms with said re-hydrating liquid to produce viable organisms.

* * * * *